(12) United States Patent
Kaneda

(10) Patent No.: US 7,938,015 B2
(45) Date of Patent: May 10, 2011

(54) MATERIAL TESTING MACHINE

(75) Inventor: Masaki Kaneda, Kyoto (JP)

(73) Assignee: Shimadzu Corporation, Kyoto-shi, Kyoto (JP)

( * ) Notice: Subject to any disclaimer, the term of this patent is extended or adjusted under 35 U.S.C. 154(b) by 153 days.

(21) Appl. No.: 12/304,168

(22) PCT Filed: Jun. 12, 2006

(86) PCT No.: PCT/JP2006/311732
§ 371 (c)(1),
(2), (4) Date: Dec. 10, 2008

(87) PCT Pub. No.: WO2007/144929
PCT Pub. Date: Dec. 21, 2007

(65) Prior Publication Data
US 2010/0011873 A1   Jan. 21, 2010

(51) Int. Cl.
*G01N 3/00* (2006.01)
(52) U.S. Cl. .......................................... 73/788
(58) Field of Classification Search ................ 73/788, 73/796, 825, 816
See application file for complete search history.

(56) References Cited

U.S. PATENT DOCUMENTS

| | | | |
|---|---|---|---|
| 3,203,232 A * | 8/1965 | Lehnig, Jr. ........................ 73/796 |
| 4,836,494 A | 6/1989 | Johnsen | |
| 5,263,373 A * | 11/1993 | Wakabayashi et al. ......... 73/788 |
| 5,413,306 A | 5/1995 | Mahoney et al. | |
| 5,677,494 A * | 10/1997 | Keener et al. ................... 73/810 |
| RE36,392 E | 11/1999 | Mahoney et al. | |
| 7,137,306 B2 * | 11/2006 | Ferguson et al. ............... 73/818 |
| 7,757,564 B2 * | 7/2010 | Kaneda ........................... 73/796 |

FOREIGN PATENT DOCUMENTS

| | | |
|---|---|---|
| EP | 0262208 A1 | 4/1988 |
| JP | 59-048633 A | 3/1984 |
| JP | 63-503052 A | 11/1988 |
| JP | 08-114536 A | 5/1996 |
| JP | 2002-139007 A | 5/2002 |

OTHER PUBLICATIONS

Germany Office Action dated Jun. 11, 2010, issued in corresponding Germany Patent Application No. 112006003923.7.

* cited by examiner

*Primary Examiner* — Lisa M Caputo
*Assistant Examiner* — Octavia Davis
(74) *Attorney, Agent, or Firm* — Westerman, Hattori, Daniels & Adrian, LLP

(57) ABSTRACT

The present invention includes: a pair of columnar members 12a and 12b disposed on both sides of a specimen SP; a crosshead 15, constructed so as to bridge the pair of columnar members 12a and 12b, that applies a load to the specimen SP by moving in a direction of a longitudinal axis of the columnar members 12a and 12b; and a support pole 35 at which a mounting fixture is to be attached, that extends in the direction of the longitudinal axis circumjacent the pair of columnar members 12a and 12b. The support pole 35 is provided with a sliding attachment unit 35b to 35d that extends in the direction of the longitudinal axis and slides a mounting fixture for use in material testing to change a position at which the mounting fixture is attached.

6 Claims, 14 Drawing Sheets

(a)

(b)

(a)

(b)

(a)

(b)

(c)

(a)

(b)

(a)

(b)

(a)

(b)

(a)

(b)

(c)

(a)

(b)

(c)

(a)

(b)

US 7,938,015 B2

MATERIAL TESTING MACHINE

TECHNICAL FIELD

The present invention relates to a material testing machine which applies a load to a test piece through a crosshead.

BACKGROUND ART

Conventionally, a material testing machine is known in which right and left driving screws for elevating a crosshead are driven by a motor to elevate the crosshead to exert a test force on a specimen and the specimen is evaluated (for instance, see Patent Document 1). This kind of material testing machine is sometimes used to perform tests with a mounting fixture such as an illumination lamp or a protection shield being fitted to a main body of the material testing machine. For instance, the material testing machine disclosed in Patent Document 1 includes a crosshead that is moved up and down through right and left drive screws. The drive screws are concealed by support poles each having a surface in which there is formed a slot of a T-shape in cross-section that permits mounting fixtures to be fitted therethrough. The support poles are formed by extrusion of aluminum.

Patent Document 1: U.S. Pat. No. 36,392

SUMMARY OF THE INVENTION

Problems to be Solved by the Invention

However, the one disclosed in Patent Document 1 above has support poles formed by extrusion, and the cover for concealing the drive screws becomes expensive.

Means for Solving the Problem

A material testing machine according to the present invention includes: a pair of columnar members disposed on both sides of a specimen; a crosshead, constructed so as to bridge the pair of columnar members, that applies a load to the specimen by moving in a direction of a longitudinal axis of the columnar members; and a support pole at which amounting fixture is to be attached, that extends in the direction of the longitudinal axis circumjacent the pair of columnar members, wherein: the support pole is provided with a sliding attachment unit that extends in the direction of the longitudinal axis and slides a mounting fixture for use in material testing to change a position at which the mounting fixture is attached.

It is preferable that the support pole is provided with a plurality of the sliding attachment units.

In this case, the plurality of the sliding attachment units may be disposed on surfaces of the support pole facing in mutually different directions, respectively.

It is also possible to include a pole cover that conceals the pair of columnar members, and the support pole may be detachably provided to a surface of the pole cover.

A connector that connects a plurality of the support poles with each other in a direction vertical to the direction of the longitudinal axis may be further provided.

Advantageous Effect of the Invention

According to the present invention, a support pole at which a mounting fixture is to be fitted is disposed around a pair of columnar members for supporting a crosshead and the support pole is provided with a slidable mounting unit for fitting the mounting fixture in the longitudinal direction thereof. As a result, it is unnecessary to form a slot for fitting a mounting fixture in the surface of the pole cover, so that the material testing machine can be constructed at low cost.

Figure 1:
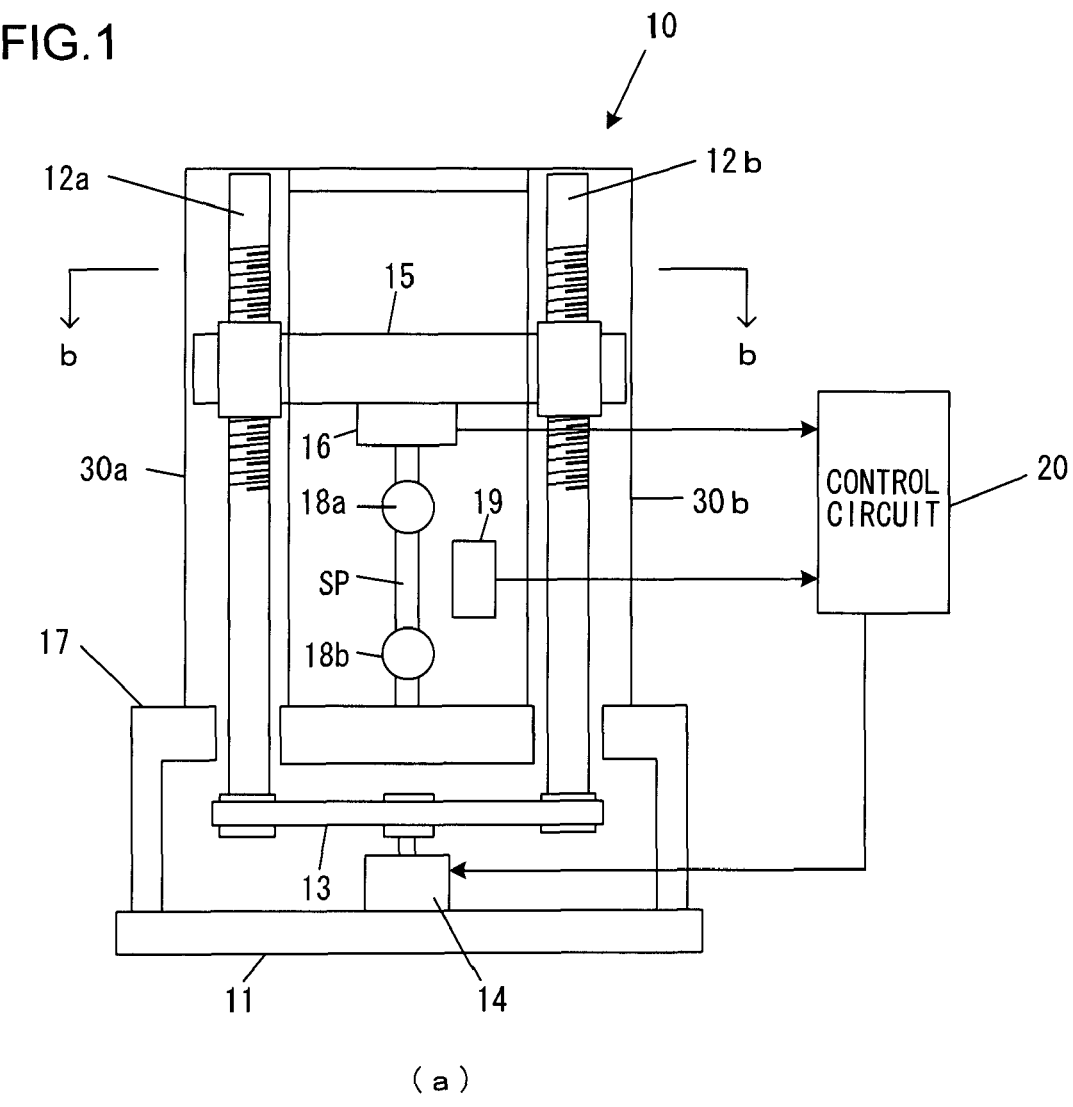
FIG. 1(a) is a schematic configuration diagram showing a material testing machine according to an embodiment of the present invention and FIG. 1(b) is a b-b line cross-section of FIG. 1(a)
Figure 1:
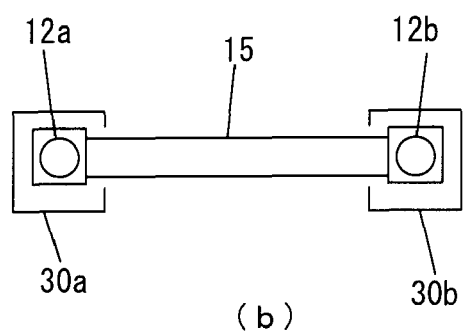
Figure 2:
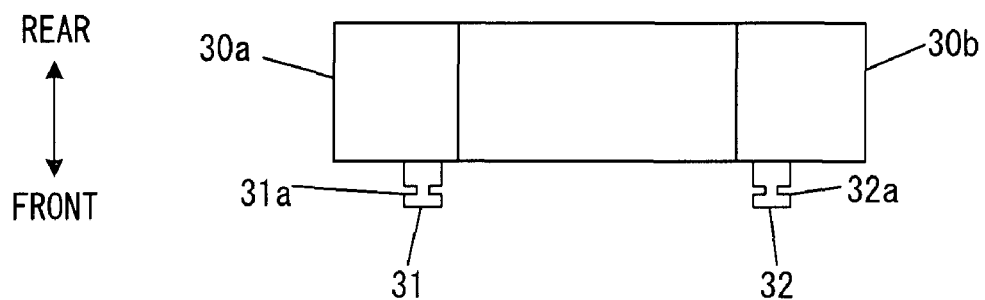
FIG. 2(a) and FIG. 2(b) are a top view and a front view, respectively, of a main body of the material testing machine according to the present embodiment, showing an appearance of a pole cover.
Figure 2:
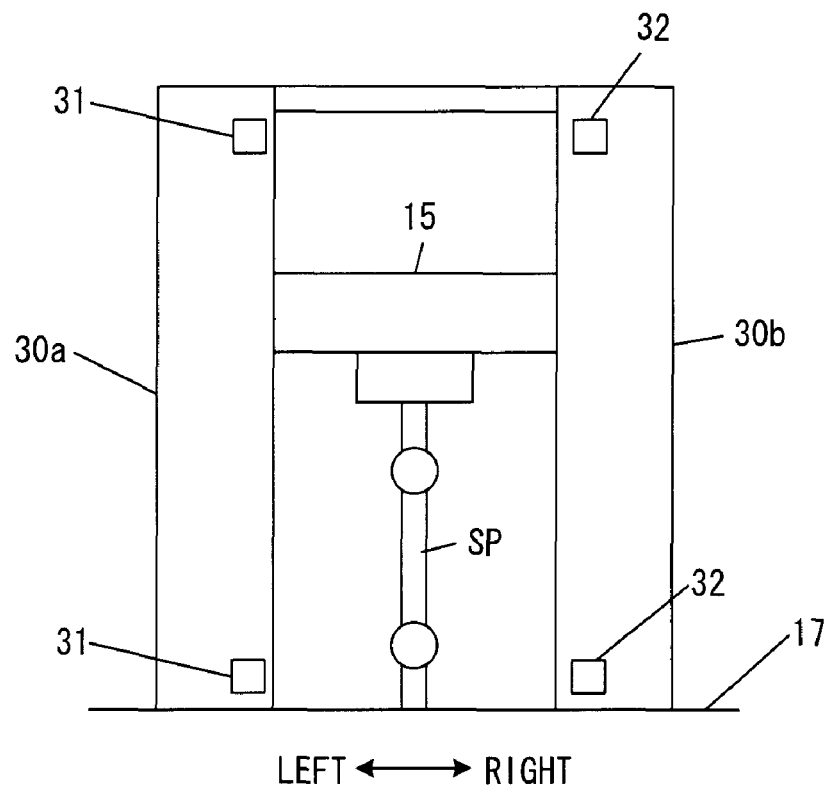

EXPLANATION OF LETTERS AND NUMERALS 12a, 12b Screw poles
15 Crosshead
30a, 30b Pole covers
35 Support pole
35a-35d T-slots
36 Connector

BEST MODE FOR CARRYING OUT THE INVENTION

The following is an explanation of a material testing machine according to an embodiment of the present invention, given in reference to FIGS. 1 to 14.

FIG. 1(a) is a diagram schematically showing the construction of the material testing machine according to the embodiment. FIG. 1(b) is a b-b line cross-sectional view of FIG. 1(a). A main body 10 of the testing machine includes a base 11, a pair of screw poles 12a, 12b that is set up on the base 11, a timing belt 13, a motor 14 that is mounted on the base 11 and rotates the screw poles 12a, 12b through the timing belt 13, a crosshead 15 elevatably held by the screw poles 12a, 12b, a table 17, upper and lower grippers 18a, 18b that grip a specimen SP between the crosshead 15 and the table 17, and pole covers 30a, 30b that cover surroundings of the screw poles 12a, 12b.

As shown in FIG. 1(b), the pole covers 30a, 30b each represent a cylindrical shape that is substantially rectangular in cross-section. The crosshead 15 bridges the screw poles 12a, 12b, penetrating through inner surfaces of the right and left pole covers 30a, 30b. Thus, dust and dirt can be prevented from entering the screw poles 12a, 12b by concealing the screw poles 12a, 12b with the pole covers 30a, 30b, respectively. On surfaces of the pole covers 30a, 30b, there are fitted rail-shaped support poles 35, respectively, at which various mounting fixtures to be detailed later are to be fitted.

The specimen SP has an upper part that is gripped by the upper gripper 18a and a lower part that is gripped by the lower gripper 18b. The upper gripper 18a is connected to the crosshead 15 through a load cell 16. The test force applied onto the specimen SP is detected by the load cell 16, and displacement between top and bottom gauge marks of the specimen SP is detected by a displacement gage 19 (for instance, a non-contact type displacement meter). Signals from the load cell 16 and the displacement meter 19 are input into a control circuit 20. The material testing is performed by controlling the driving by the motor 14 according to a signal from the control circuit 20.

FIG. 2(a) and FIG. 2(b) are a top view and a front view, respectively, of the main body 10 of the material testing machine showing the appearances of the pole covers 30a, 30b, respectively. The pole covers 30a, 30b each are provided on the surface thereof with a pair of latches 31 and 32 that are vertically arranged. The latches 31 and 32 are locked to the surfaces of pole covers 30a and 30b, respectively, with, for instance, bolts. On both right and left sides of each latch 31, 32, there is formed vertically a guide groove 31a, 32a, respectively. The latches 31 and 32 each have a T-shaped head as shown in FIG. 2(a). The support poles 35 are brought into engagement with the latches 31 and 32, respectively.

Figure 3:
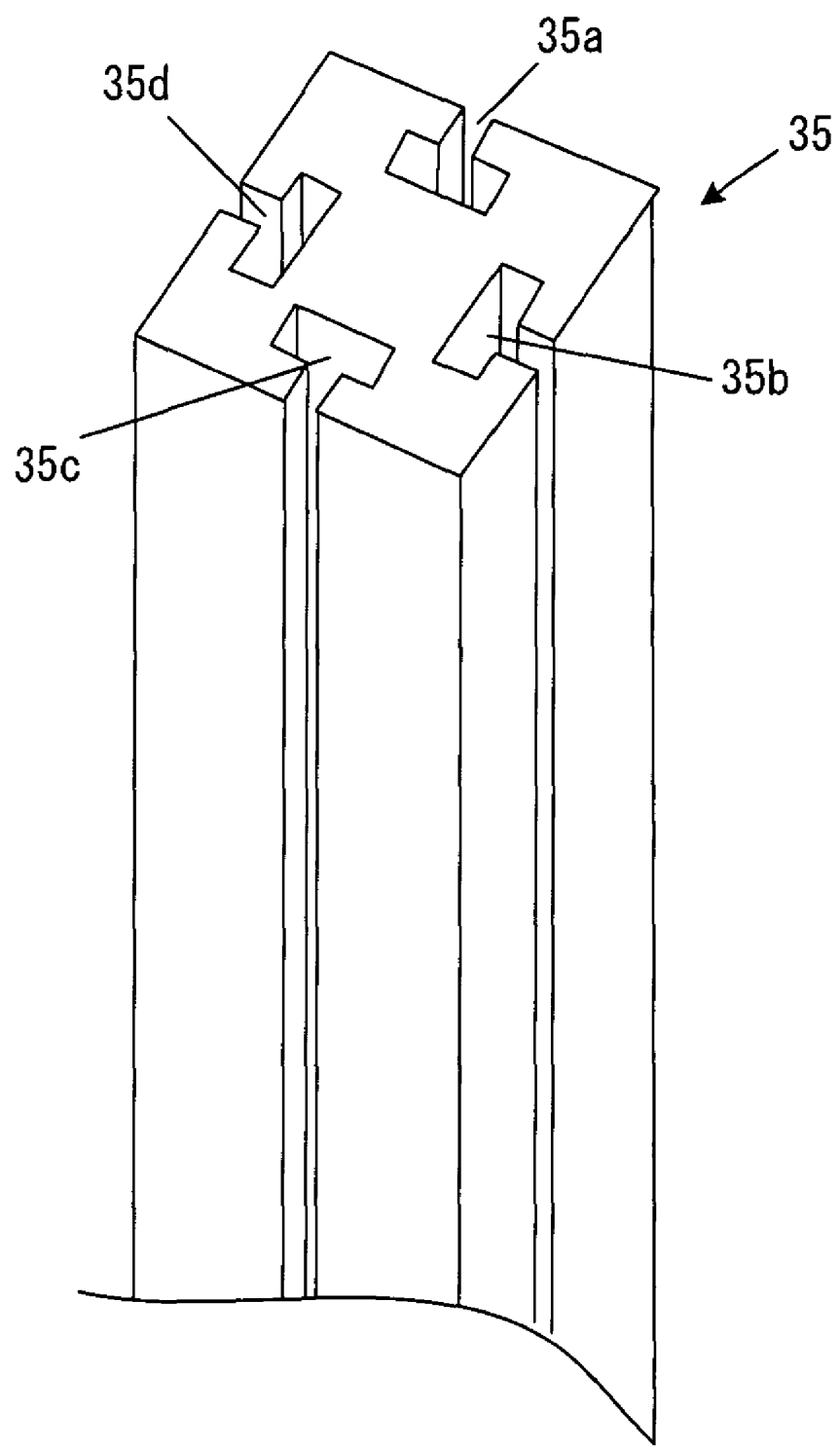
FIG. 3 is a perspective view showing the shape of a support pole according to one embodiment.
Figure 4:
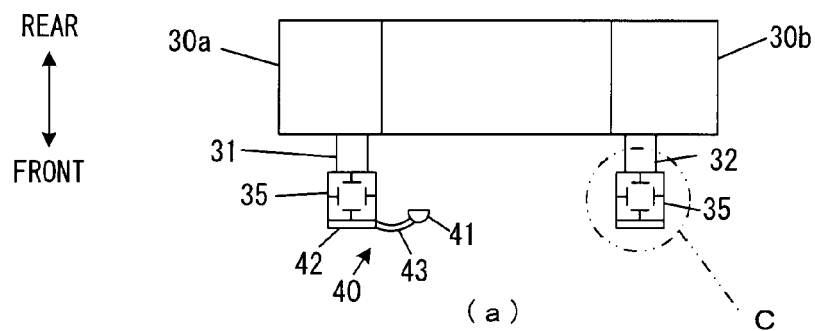
FIGS. 4(a) and 4(b) are a top view and a front view, respectively, of the main body of the material testing machine showing a state where the support pole of FIG. 3 is mounted.
FIG. 4(c) is an enlarged view of the part C in FIG. 4(a)
Figure 4:
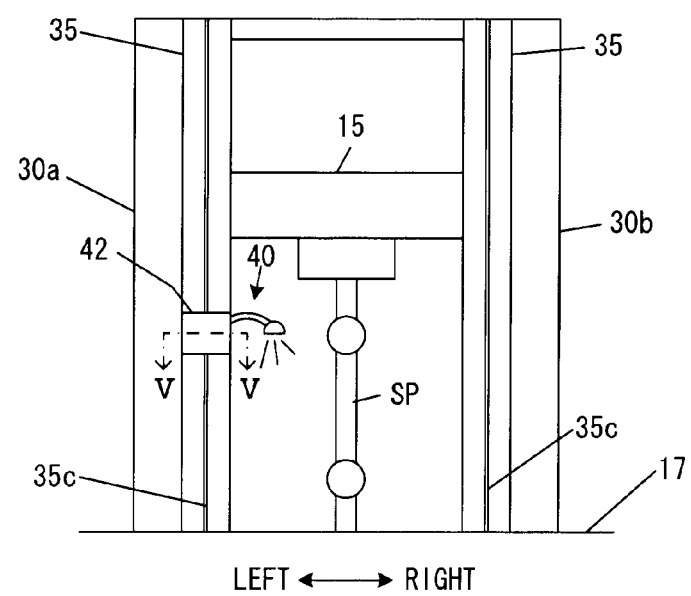
Figure 4:
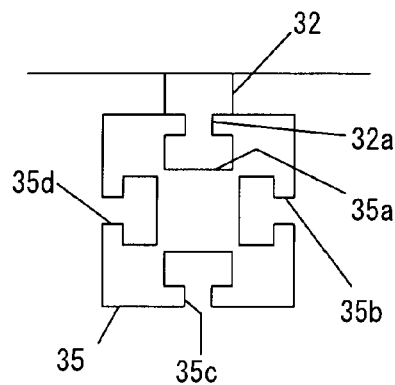

FIG. 3 is a perspective view showing the shape of the support pole 35. The support pole 35 extends in the longitudinal direction, representing in whole a substantially prismatic shape. It has four surfaces in the circumferential direction, with the surfaces being formed with T-shaped slots (T-slots) 35a-35d, respectively, over the whole length along the longitudinal direction. One T-slot 35a from among them is a slot for fitting therein a pole cover. The support poles 35 are lowered from above the latches 31 and 32 of the pole covers 30a, 30b so as to fit respective T-shaped heads of the upper and lower latches 31 and those of the upper and lower latches 32 in the T-shaped slots 35a, respectively. As a result, the support poles 35 are locked on the surfaces of the pole covers 30a and 30b, respectively, through the respective latches 31 and 32 as shown in FIG. 4 and the engagement is locked. Then, the lower end surface of each support pole 35 comes in contact with an upper surface of the table 17, and each support pole 35 is locked vertically, too.

FIGS. 4(a) and 4(b) are a top view and a front view, respectively, of the main body 10 of the material testing machine, showing a state where the support poles 35 are fitted. FIG. 4(c) is an enlarged view of the part C in FIG. 4(a). The mounting fixtures for various tests can be fitted in the T-slot 35c provided on the front surface of the support pole 35 and in the T-slots 35b and 35d provided on the right and left side surfaces of the support pole 35. FIG. 4 shows an example in which a light 40 for illumination is fitted in the T-slot 35c in the front surface of the support pole. A main body 41 of the light is disposed to a head of an arm 43, which extends from a base board 42. The base board 42 is locked to the support pole 35 through the T-slot 35c.

Figure 5:
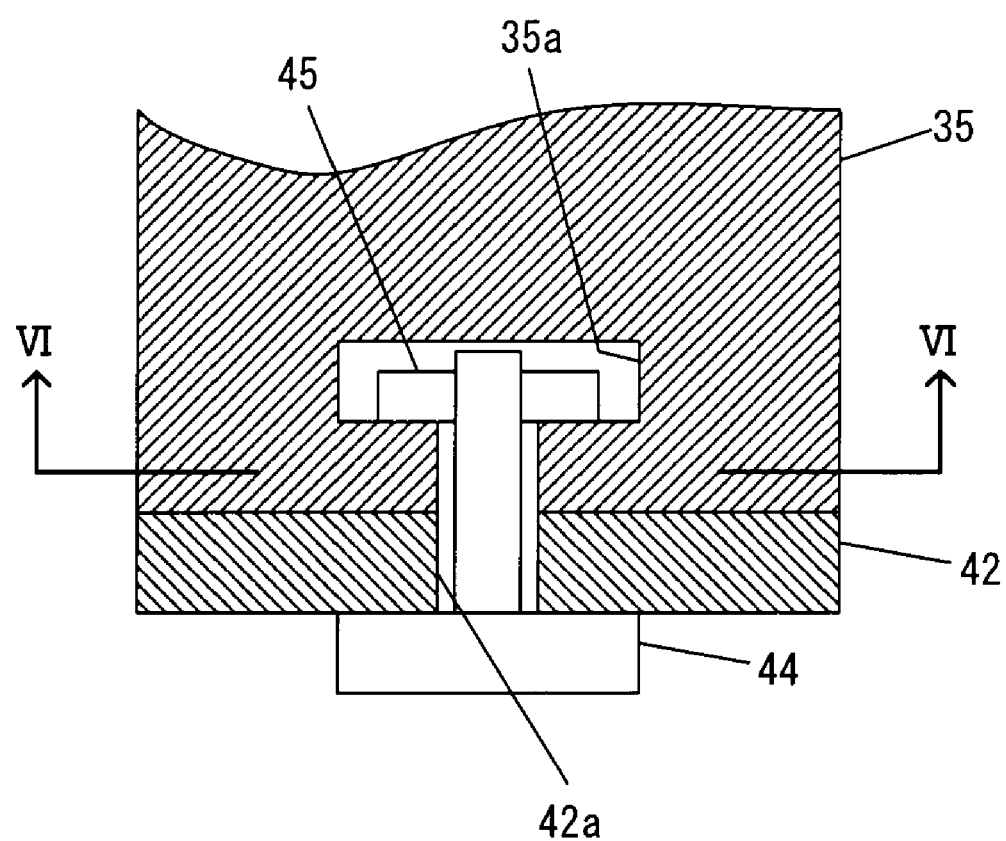
FIG. 5 is a sectional view taken along the line V-V in FIG. 4(b)
Figure 6:
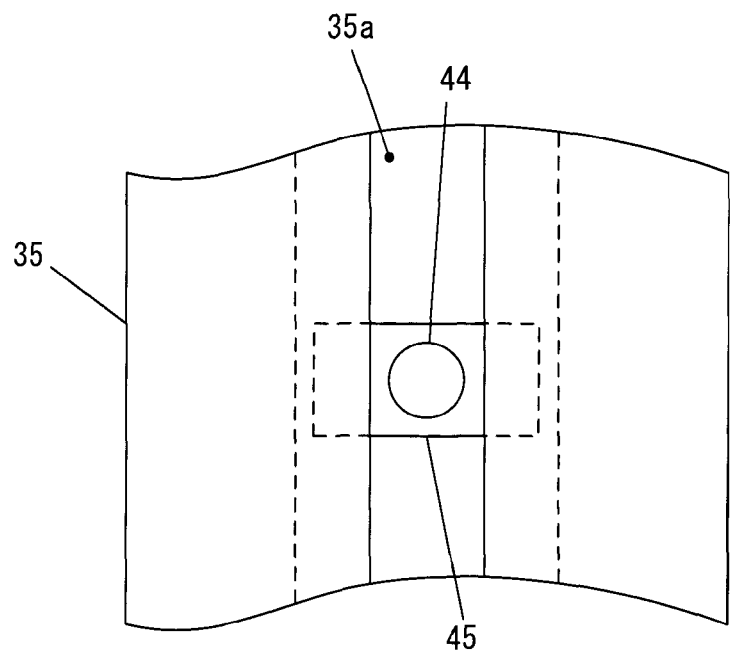
FIG. 6 is a cross-sectional view taken along the VI-VI line in FIG. 5.
Figure 6:
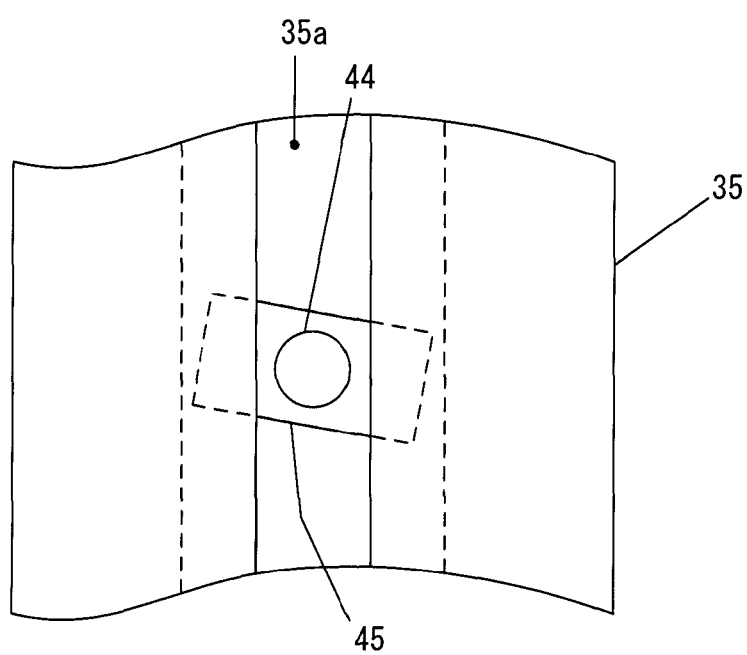
Figure 7:
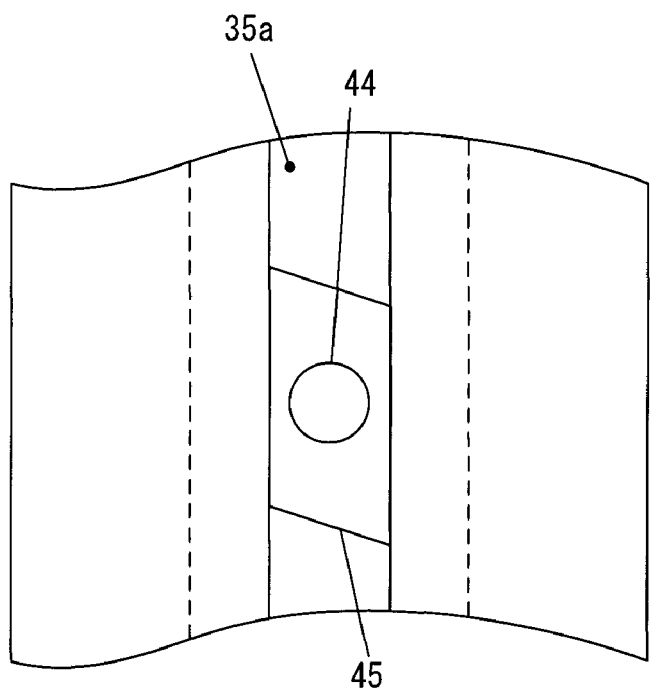
FIG. 7 is a diagram showing a modification of the machine of FIG. 6.
Figure 7:
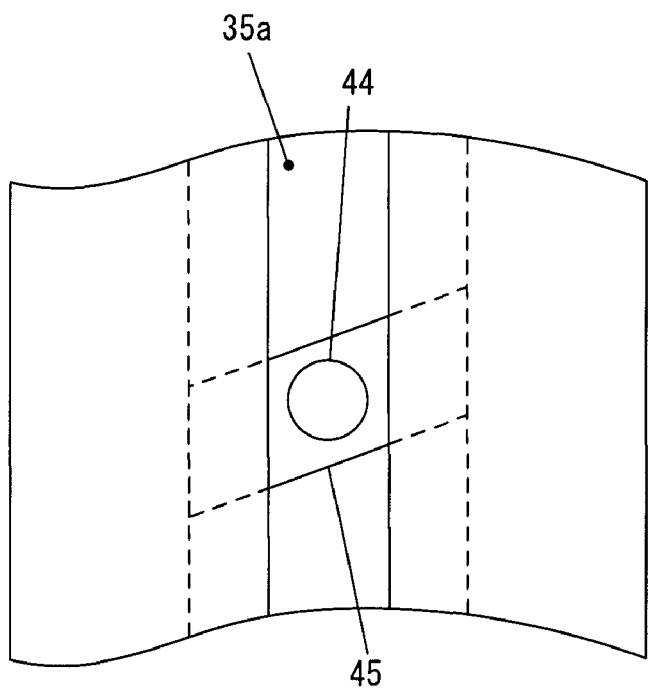

FIG. 5 is a V-V line cross-sectional view of FIG. 4(b) showing a state where the base board 42 is fixed. FIG. 6 is a VI-VI line cross-sectional view of FIG. 5. A through-hole 42a for inserting therein a bolt is formed in the base board 42. The bolt 44 penetrating the through-hole 42a is threadably mounted in a nut 45 disposed inside the T-slot 35a. The bolt 44 and the nut 45 are inserted in the through-hole 42a from the upper end surface of the support pole 35. The nut 45 is of a substantially rectangular shape as shown in FIG. 6(a). Therefore, when the nut 45 rotates, the corners thereof come in contact with the end surface of the T-slot 35a as shown in FIG. 6(b) and the rotation of the nut 45 is obstructed. As a result, the bolt 44 can be tightened without holding the nut 45 with a tool or the like and the base board 42 can be fastened and locked to the surface of the support pole 35.

Figure 8:
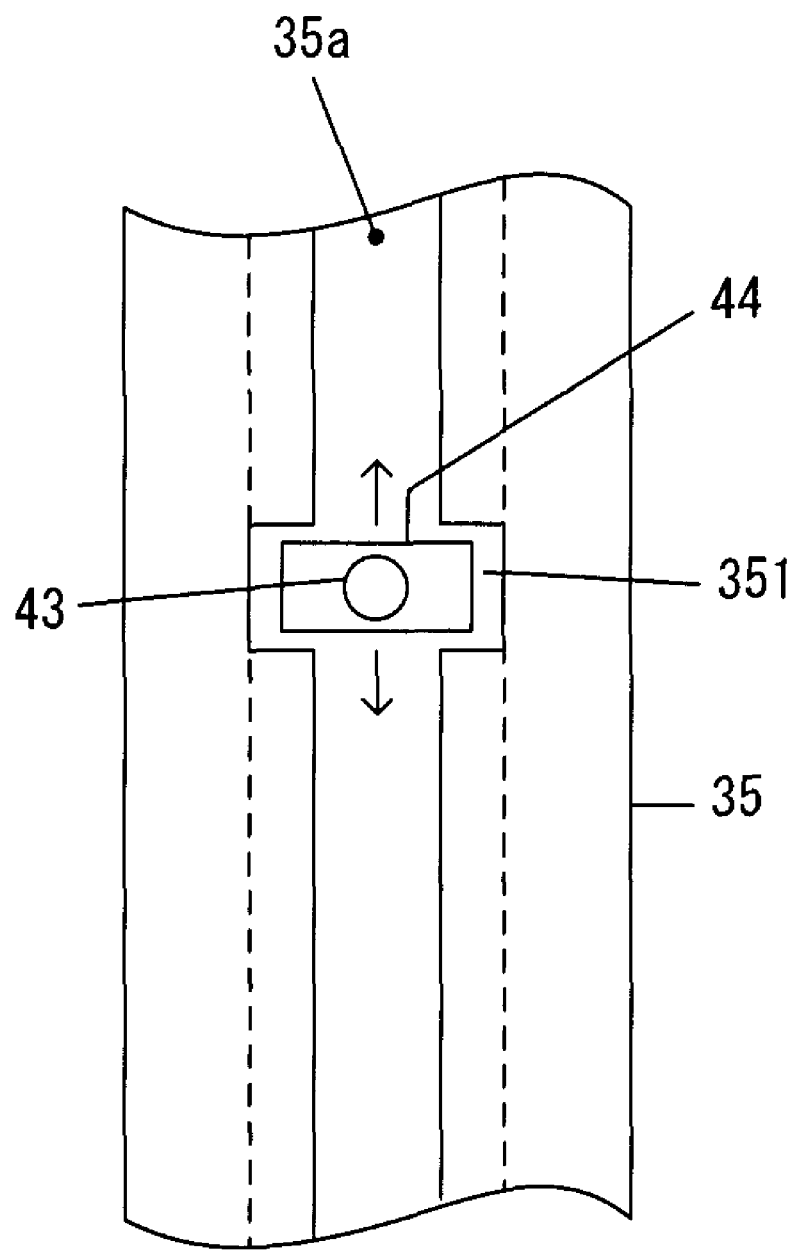
FIG. 8 is a diagram showing another modification of the machine of FIG. 6.
Figure 9:
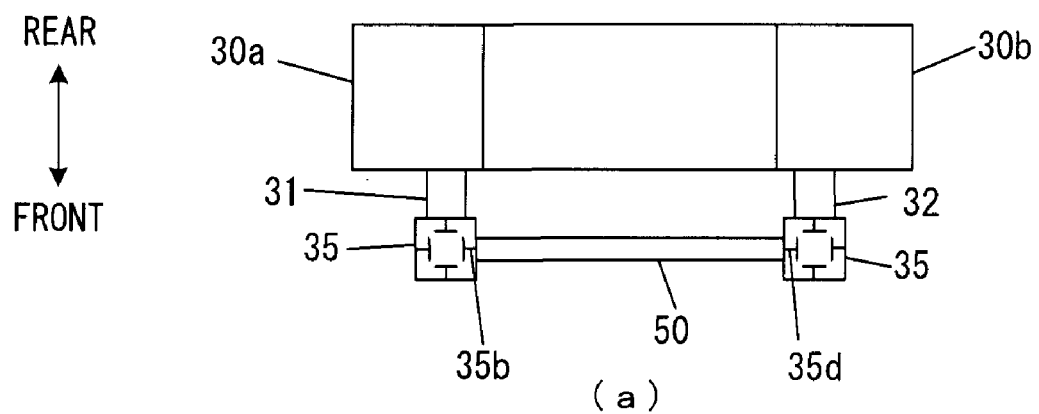
FIG. 9(a) and FIG. 9(b) are a top view and a front view, respectively, of the main body of the material testing machine, showing an example in which a cover for preventing scattering is fitted to the support pole shown in FIG. 4.
Figure 9:
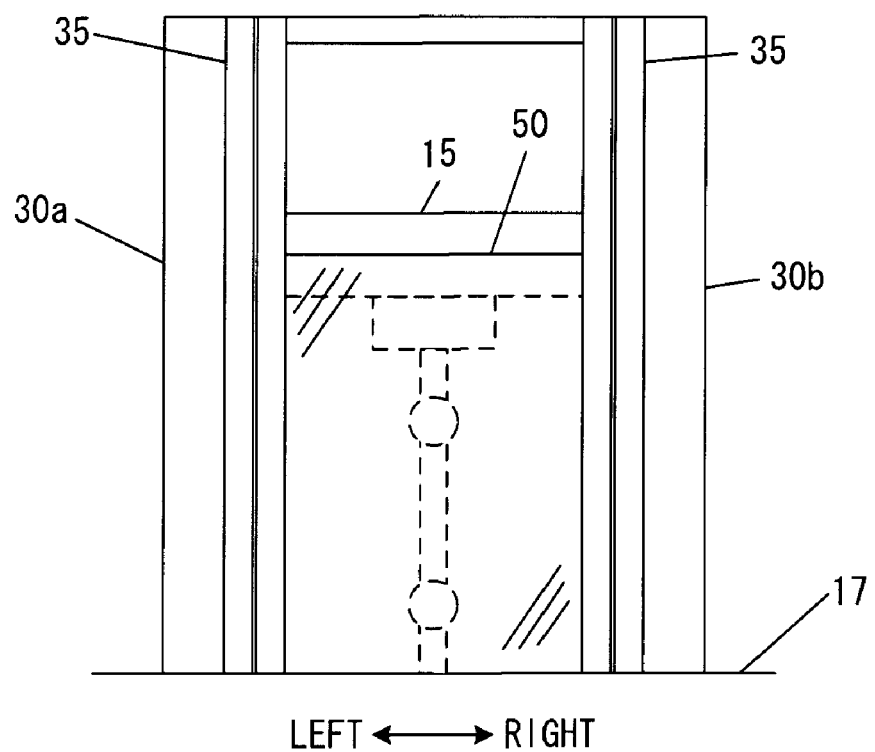

On this occasion, in a state where the bolt 44 is loosened, the base board 42 can slide vertically together with the bolt 44 and the nut 45 according to the T-slot 35a, so that the base board 42 can be locked to any desired position. The base board 42 can be disengaged from the top of the T-slot 35a by sliding the base board 42 upward with the bolt 44 loosened. If the nut 45 is assumed to be an elongate parallelogram or rectangle as shown in FIG. 7(a), it can be inserted through the surface of the support pole to the bottom end of the T-slot 35a, i.e., without need to insert the nut 45 from the upper end surface of the support pole 35, so that the base board 42 can be easily fitted. In this case too, the edges of the nut 45 come into contact with the end surface of the T-slot 35a as shown in FIG. 7(b), so that the rotation of the nut 45 is obstructed. The T-slot 35a may be constructed to have a widened portion 351 widened as shown in FIG. 8 and the nut 44 may be inserted through the widened portion 351 into the T-slot 35a, and then the nut 44 together with the base board 42 may be slid vertically.

To the support pole 35, there may be fitted not only the light 40 but also various other mounting fixtures to be used at the time of material testing, such as an extensometer 19 (for instance, a CCD camera), a cover for preventing the scattering of the specimen SP, a marker for specifying the position of the crosshead 15, a dough box, clamps for wires, cables, etc., and an operation panel. That is, a plurality (two in this example) of support poles 35 is fitted to the surface of each pole cover, and a plurality (three in this example) of T-slots 35b-35d for fitting therein mounting fixtures is formed in each support pole 35. Therefore, the plurality of mounting fixtures can be vertically fitted at any desired position on each support pole without mutual interferences.

FIG. 9(a) and FIG. 9(b) are a top view and a front view, respectively, of the main body 10 of the material testing machine, showing an example in which a cover 50 for preventing the scattering is fitted to the support pole 35. The cover 50 for preventing scattering extends between the right and left support poles 35 ranging from the upper end surface of the table 17 to near the crosshead 15 so as to close the front side of the specimen SP. Both the right and left ends of the cover 50 are formed so as to have a T-shaped cross section, and the cover 50 is engaged with the support poles 35 such that it can slide according to the T-slots 35b and 35d provided in respective inside surfaces of the support poles 35. As a result, when the specimen SP is to be mounted to or dismounted from the grippers 18a and 18b, it only has to slide the cover 50 upward and it is unnecessary to disengage the cover 50. Therefore, the material testing can be efficiently performed.

Figure 10:
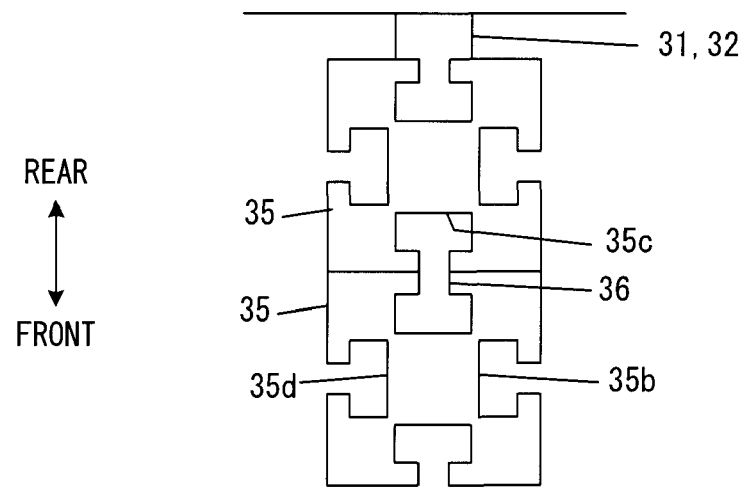
FIG. 10 is a diagram showing a modification of the machine of FIG. 9.
Figure 10:
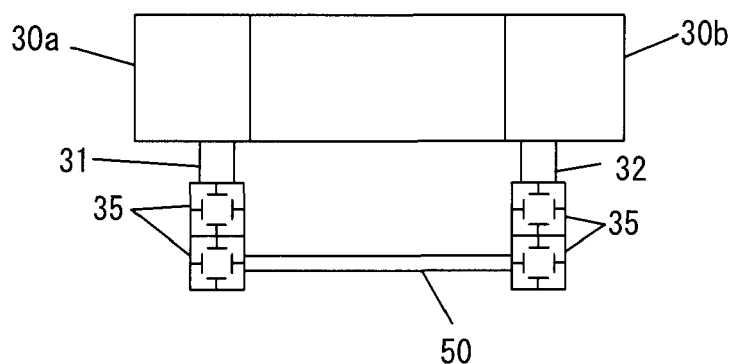
Figure 10:
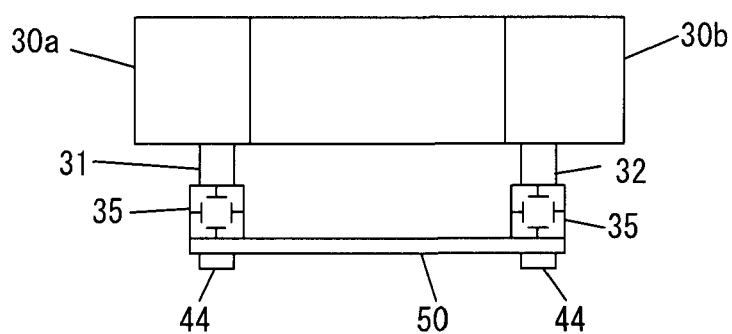
Figure 11:
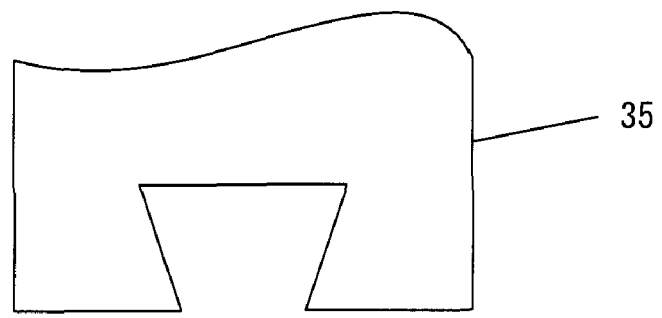
FIG. 11 is a diagram showing a modification of the cross-sectional shape of the support pole.
Figure 11:
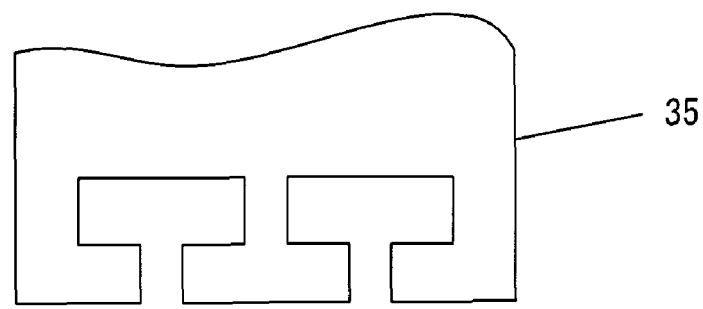
Figure 11:
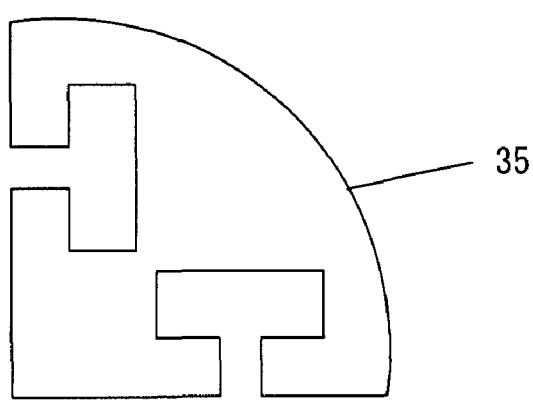

A connector 36 that has an H-shaped cross section can be engaged with the T-slot 35c in front of the support pole 35 as shown in FIG. 10(a), and another support pole 35 can be additionally connected thereto through the connector 36. As a result, the cover 50 for preventing scattering can be mounted by being deviated forward only by the length of the support pole 35 as shown in FIG. 10 (b). Accordingly, the front side of the specimen SP can be covered regardless of the shape of the specimen SP. The cover 50 can be mounted in front of the support pole 35 through the bolt 44 as shown in FIG. 10(c) instead of engaging the right and left edges of the cover 50 with the T-slots 35b and 35d. In this case, it only has to screw together the bolt 44 to the nut 45 in the T-slot 35c similarly to the case shown in FIG. 5, and, as a result, the cover 50 can be locked to any desired position on the support pole 35 in the vertical direction.

The following operational effects can be achieved in the embodiment described above.

(1) On the surfaces of the pole covers 30a and 30b, there are attached the support poles 35 having formed therein the T-slots 35a-35d in the longitudinal direction and various mounting fixtures for testing, such as the illumination light 40, are to be mounted on the support pole through the T-slots 35 b-35d. As a result, the cost can be reduced since the pole covers 30a and 30b need not be processed to provide T-slots therein.

(2) The material testing machine has a good appearance since the pole covers 30a and 30b, which are concealment members for the screw poles 12a, 12b, need not be formed of slotted holes etc.

(3) Since a plurality of T-slots 35a-35d is disposed to the support pole 35, a plurality of mounting fixtures can be mounted on any desired position thereon in the vertical direction without mutual interferences therebetween.

(4) The direction of the mounting fixture can be easily changed since the T-slot 35a-35d are disposed to different surfaces of the support pole 35, respectively.

(5) Since the support poles 35 are detachably disposed to the surfaces of the pole covers 30a and 30b through the latches 31 and 32, tests can be performed in a state where the support poles 35 are disengaged when the mounting fixtures need not be attached. As a result, the material testing machine can meet various needs of customers. Moreover, the support poles 35 can be mounted later as optional parts.

(6) Since it is only necessary to attach the latches 31 and 32 to the pole covers 30a and 30b, an increase in the manufacturing cost for pole covers 30a and 30b can be suppressed.

(7) The latches 31 and 32 do not become obstructive in a state where the support poles 35 are detached since they are attached to the upper and lower ends of the respective pole covers 30a, 30b.

(8) Since the T-slots 35a of the support poles 35 are engaged with the latches 31 and 32 to support the support poles 35, it is easy to mount and dismount the support poles 35.

(9) Since the support poles 35a can be connected to each other in the direction perpendicular to the longitudinal direction through the connector 36 (FIG. 10), the mounting fixtures can be attached to the pole covers such that they are deviated forward from the specimen according to the size of the specimen SP.

In the above-mentioned embodiment, the lower end surface of the support pole 35 is brought into contact with the upper end surface of the table 17. However, the position of the support pole 35 may be restricted by providing the pole covers 30a, 30b with stopper portions, respectively, below the lower latches 31, 32 to prevent the movement of the support pole 35 from the stopper portions downward. The support poles 35 are engaged to the latches 31 and 32, respectively, to attach the support poles 35 to the surfaces of the pole covers 30a, 30b. However, the support poles 35 may be separately provided with respective brackets so that they can be locked through the brackets to the surfaces of the pole covers 30a and 30b, respectively, with screws or the like. Alternatively, the latches 31 and 32 may be omitted. That is, the support structure of the support pole 35 as the support pole for attaching a mounting fixture is not limited to the one mentioned above.

The support pole 35 is provided with the T-slots 35a-35d in the longitudinal direction and mounting fixtures are made slidable along the T-slots 35a-35d to change the positions at which the mounting fixtures are attached. However, the slidable attachment part may be of a shape other than the T-slot as shown in, for instance, FIG. 11(a). Although the T-slots 35a-35d are provided on four surfaces, respectively, of the support pole 35, the T-slot may be provided on only one surface, on two surfaces, or on three surfaces of the support pole 35 in the circumferential direction thereof. A plurality of T-slots may be disposed to one surface as shown in FIG. 11(b). The cross-sectional shape of the support pole 35 may be other than rectangular. It may be of, for instance, a sectorial shape as shown in FIG. 11(c). Alternatively, it may assume the shape of a circle, a triangle, a pentagon or higher polygon. The shape of connector 36 is not limited to the one mentioned above.

Figure 12:
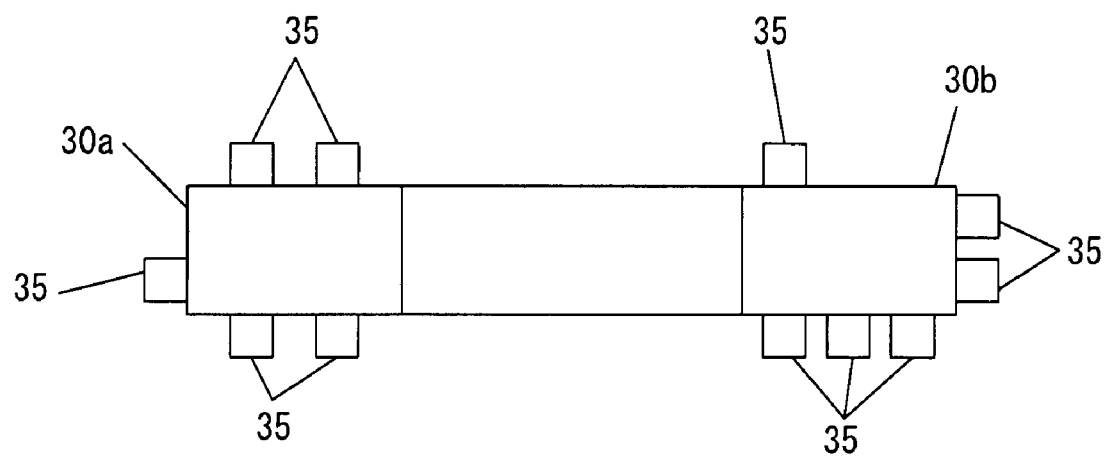
FIG. 12 is a diagram showing a modification concerning the fitting position of the support pole in the circumferential direction.
Figure 13:
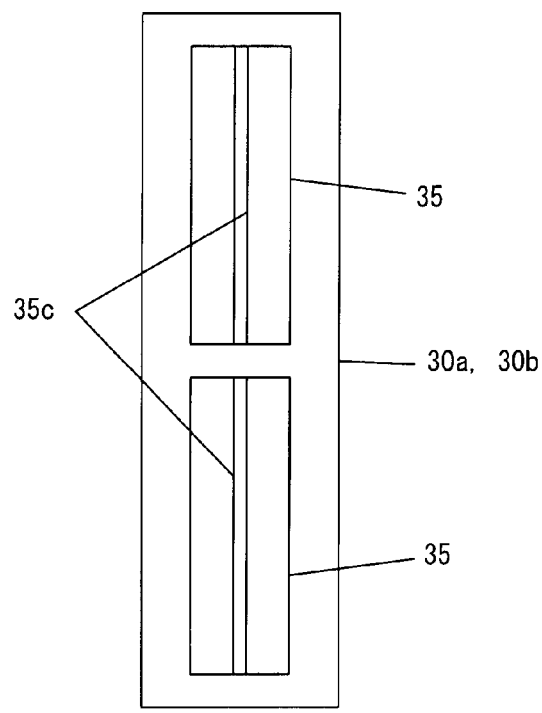
FIG. 13 is a diagram showing a modification concerning the fitting position of the support pole in the vertical direction.
Figure 13:
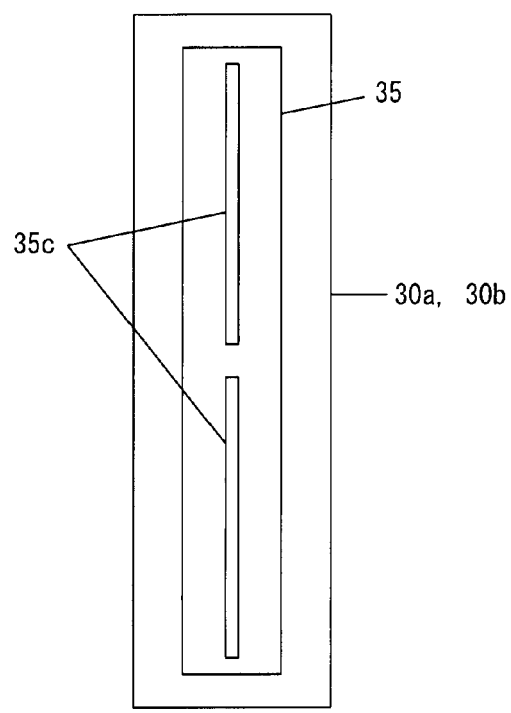

The support poles 35 are attached to the front surfaces of the pole covers 30a and 30b, respectively. However, the positions at which the support poles 35 are attached are not limited to those mentioned above. For instance, more support poles 35 may be attached as needed as shown in FIG. 12. The support poles 35 are disposed over the whole length along the direction of the longitudinal axis of pole covers 30a and 30b. However, the support poles 35 may be disposed only a part of the whole length of the pole covers 30a and 30b in the longitudinal direction. Moreover, a plurality of support poles 35 may be disposed in series in the longitudinal direction as shown in FIG. 13(a). The T-slots 35a-35d are formed in the support pole 35 over the whole length of the support pole 35 in the longitudinal direction thereof. However, the T-slots may be formed in only a part of the whole length of the support pole 35 in the longitudinal direction thereof. Moreover, a plurality of slots may be disposed in series in the support pole 35 in the longitudinal direction thereof as shown in FIG. 13(b).

As mentioned above, explanation has been made on the material testing machine in which the crosshead 15 is elevated by rotation of a pair of screw poles 12 to apply a load to the specimen SP and the support poles 35 are attached to the main body 10. However, the support poles 35 can be attached to the main body of a material testing machine in which a load is added to the specimen SP by other loading means such as, for instance, a hydraulic actuator. That is, the support poles 35 can be attached to the main body of a material testing machine that includes no pole covers 30a, 30b.

Figure 14:
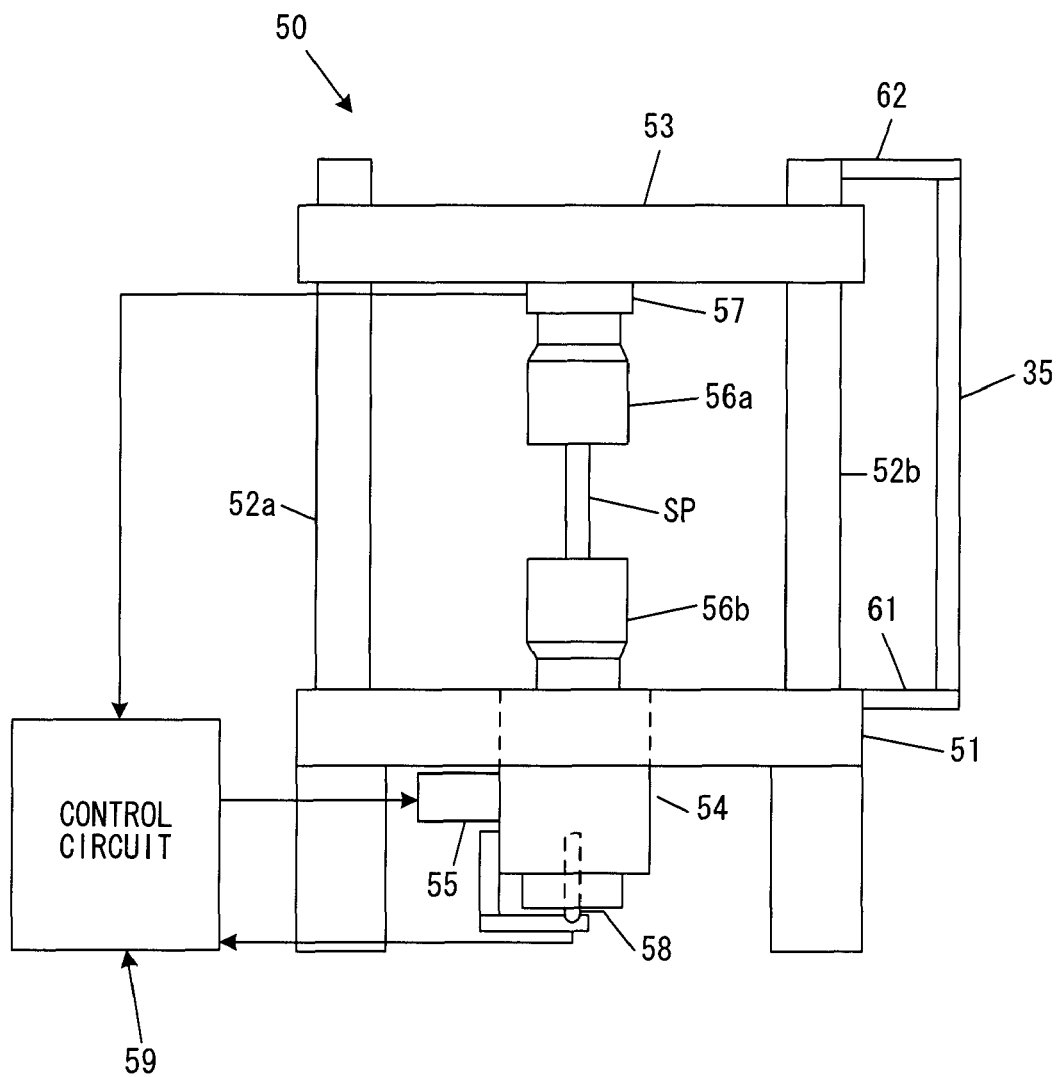
FIG. 14 is a diagram showing a modification of the machine of FIG. 1.

FIG. 14 shows an example of another material testing machine. The main body 50 of the material testing machine shown in FIG. 14 includes a base 51, support poles 52a, 52b set upright to both sides of the base 51, a crosshead 53 held by the support poles 52a, 52b, a hydraulic cylinder 54 that applies a load to a specimen SP, a servo valve 55 that controls the driving of the hydraulic cylinder 54, and an upper gripper 56a and a lower gripper 56b that hold the specimen SP between the crosshead 53 and the base 51. The lower gripper 56b is connected to a piston rod of the hydraulic cylinder 54 and the displacement of the piston rod of the hydraulic cylinder 54 is detected by a displacement meter 58. A control circuit 59 outputs a control signal corresponding to signals from a load cell 57 and the displacement meter 58 to the servo valve 55, and controls the testing force urged onto the specimen SP.

The support pole 35 is set upright to the side of the support pole 52b, and the support pole 35 is supported by the base 51 and the support pole 52b through brackets 61, 62. As a result, regardless of the presence of the pole covers 30a, 30b, the mounting fixtures can be attached through the support pole 35. This improves the facility of the machine. Any structure may be adopted to attach the support pole 35, if the support pole 35 extends in the direction of the longitudinal axis circumjacent the support pole 52a or 52b, respectively. In the above-mentioned embodiments, the support pole 35 is attached to the material testing machine in which a load is vertically added to the specimen SP such that the support pole 35 is attached substantially in parallel to the axis of loading. However, the support pole 35 may similarly be attached substantially in parallel to the axis of loading to a material testing machine in which a load is added to the specimen SP along the horizontal direction. Therefore, the direction of attaching the support pole 35 is not limited to the one mentioned above.

Namely, as long as the features and functions of the present invention are realized, the material testing machine according to the present invention is not limited to the examples presented in the above-mentioned embodiments.

The invention claimed is:

1. A material testing machine comprising:
    a pair of columnar members disposed on both sides of a specimen;
    a pole cover to conceal a columnar member;
    a crosshead, constructed so as to bridge the pair of columnar members, that applies a load to the specimen by moving in a direction of a longitudinal axis of the columnar members; and
    a support pole that is detachably attached to a surface of the pole cover and to which a mounting fixture is to be attached, the support pole extending in the direction of the longitudinal axis circumjacent the pair of columnar members; and
    a sliding attachment unit that is slidably attached to a surface of the support pole and that attaches a mounting fixture for use in material testing to the support pole, wherein the sliding attachment unit slides along the support pole in the direction of the longitudinal axis and slides the mounting fixture for use in material testing to change a position at which the mounting fixture is attached.

2. A material testing machine according to claim 1, wherein:
    the support pole is provided with a plurality of the sliding attachment units.

3. A material testing machine according to claim 2, wherein:
    the plurality of the sliding attachment units are disposed on surfaces of the support pole facing in mutually different directions, respectively.

4. A material testing machine according to claim 3, further comprising:
    a connector that connects a plurality of the support poles with each other in a direction vertical to the direction of the longitudinal axis.

5. A material testing machine according to claim 2, further comprising:
    a connector that connects a plurality of the support poles with each other in a direction vertical to the direction of the longitudinal axis.

6. A material testing machine according to claim 1, further comprising:
    a connector that connects a plurality of the support poles with each other in a direction vertical to the direction of the longitudinal axis.

* * * * *